United States Patent [19]
Borgos et al.

[11] Patent Number: 5,654,539
[45] Date of Patent: Aug. 5, 1997

[54] LASER DOPPLER OPTICAL SENSOR FOR USE ON A MONITORING PROBE

[75] Inventors: John A. Borgos, Shoreview; Douglas G. Tomasko, Woodbury, both of Minn.

[73] Assignee: Vasamedics L.L.C., St. Paul, Minn.

[21] Appl. No.: 516,045

[22] Filed: Aug. 17, 1995

[51] Int. Cl.$^6$ .................................................. H01J 5/16
[52] U.S. Cl. ........................ 250/227.11; 250/227.31; 385/31
[58] Field of Search ..................... 250/227.11, 227.32, 250/227.14, 227.31; 385/31, 12, 44, 47, 73

[56] References Cited

U.S. PATENT DOCUMENTS

| | | | |
|---|---|---|---|
| 4,109,647 | 8/1978 | Stern et al. | 128/2.05 F |
| 4,446,715 | 5/1984 | Bailey | 73/1 R |
| 4,596,254 | 6/1986 | Adrian et al. | 128/666 |
| 4,705,047 | 11/1987 | Bailey | 128/672 |
| 4,711,246 | 12/1987 | Alderson | 128/667 |
| 4,730,622 | 3/1988 | Cohen | 128/667 |
| 4,787,396 | 11/1988 | Pidorenko | 128/667 |
| 4,856,317 | 8/1989 | Pidorenko et al. | 73/4 R |
| 4,903,707 | 2/1990 | Knute et al. | 128/748 |
| 4,924,870 | 5/1990 | Wlodarczyk et al. | 128/667 |
| 4,931,049 | 6/1990 | Klimas | 604/165 |
| 5,013,313 | 5/1991 | Surer | 606/60 |
| 5,107,847 | 4/1992 | Knute et al. | 128/675 |
| 5,247,171 | 9/1993 | Wlodarczyk et al. | 250/227.21 |
| 5,280,786 | 1/1994 | Wlodarczyk et al. | 128/634 |
| B1 4,446,715 | 9/1991 | Bailey | 73/1 R |

FOREIGN PATENT DOCUMENTS 28 51 138 A  7/1979  Germany.

OTHER PUBLICATIONS

"Intraopertive Measurement of Cortical Blood Flow Adjacent to Cerebral AVM Using Laser Doppler Velocimetry", Bruce R. Rosenblum, M.D., Robert Bonner, Ph.D., and Edward H. Oldfield, M.D., *J. Neurosurg./Volume 66/Mar., 1987*, pp. 396–399.

"Inoperative Measurement of Cerebral and Tumor Blood Flow with Laser–Doppler Flowmetry", E. Arbit, M.D., G. R. DiResta, Ph.D., R. F. Bedford, M.D., N. K. Shah, M.D., and J. H. Galicich, M.D., *Neurosurgery*, vol. 24, No. 2, pp. 166–170, Jan. 1989.

"Monitoring of Hemodynamics in Subarachnoid Hemorrhage Using Trnascranial Doppler and Laser Doppler", T. Hashimoto, N. Nakamura, T. Kanki, and S. Abe, *Advances in Neurosurgery*, Vol. 17 Ed. by R. A. Frowein, M. Brock, and M. Klinger, pp. 337–343, Jan. 1989.

"Laser Doppler Flowmetry in Neurosurgery", V. A. Fasano, R. Urciuoli, P. Bolognese, M. Fontanella, *Three–Dimensional Bioimaging Systems and Lasers in Neurosciences* (1991), *SPIE vol. 1428*, pp. 2–12, Jan. 1991.

*Primary Examiner*—Que Le
*Attorney, Agent, or Firm*—Merchant, Gould, Smith, Edell, Welter & Schmidt, P.A.

[57] ABSTRACT

A laser Doppler probe for measuring blood flow, comprising a transmit fiber, and one or more receive fibers, which are configured to direct and receive energy orthogonal to the fiber axis.

9 Claims, 3 Drawing Sheets

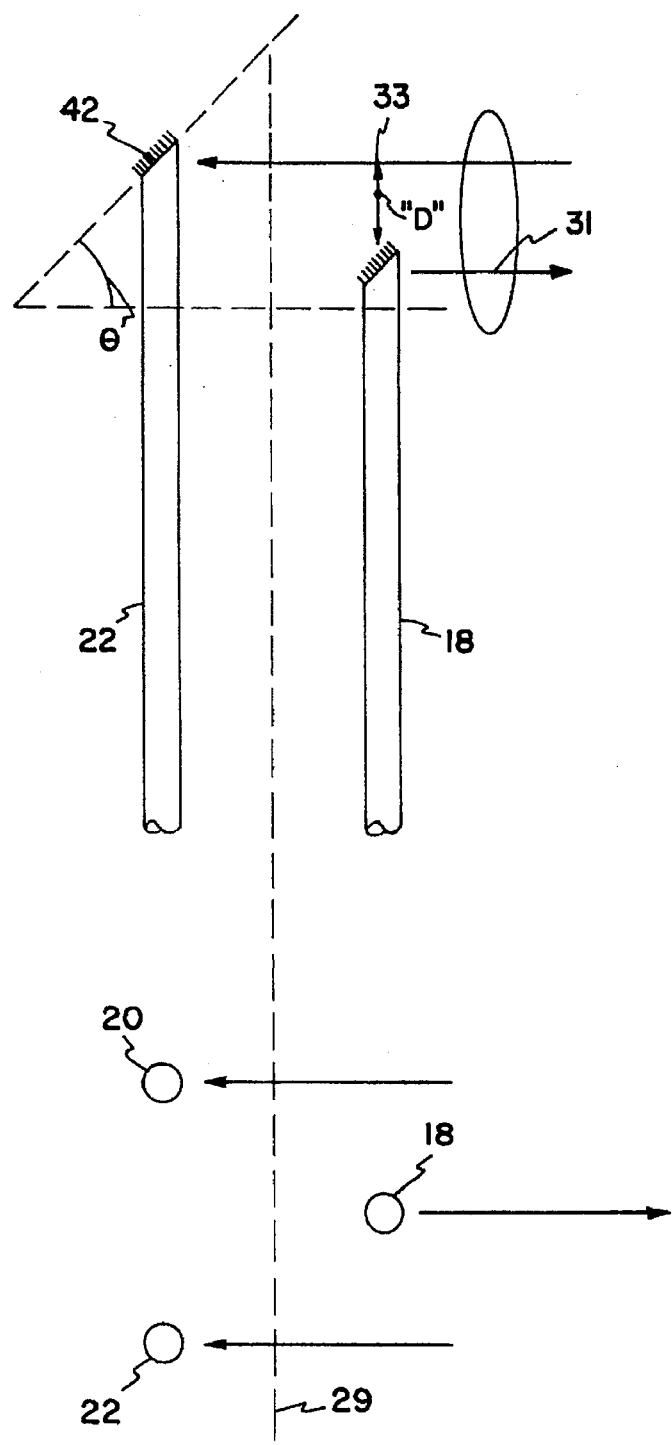
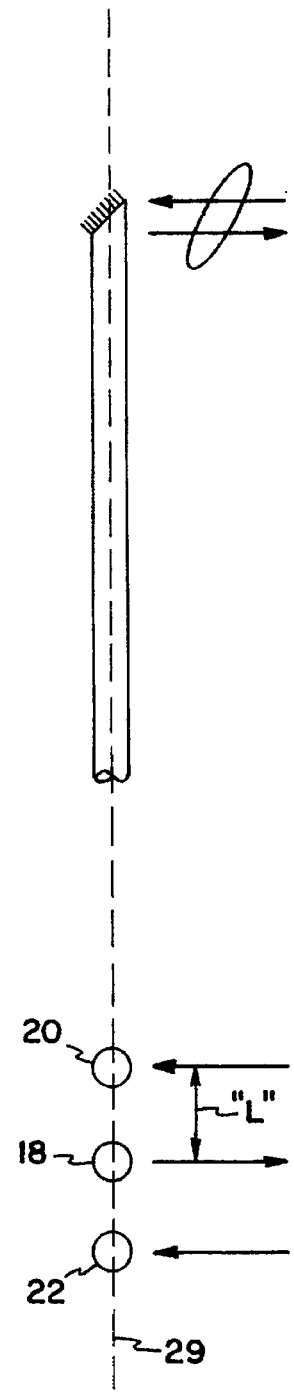
FIG. 2
FIG. 3

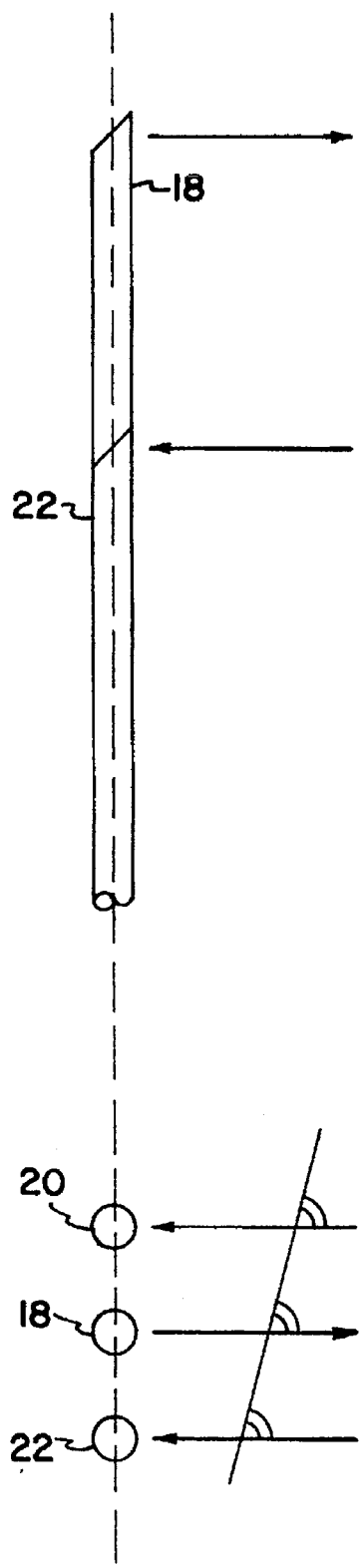
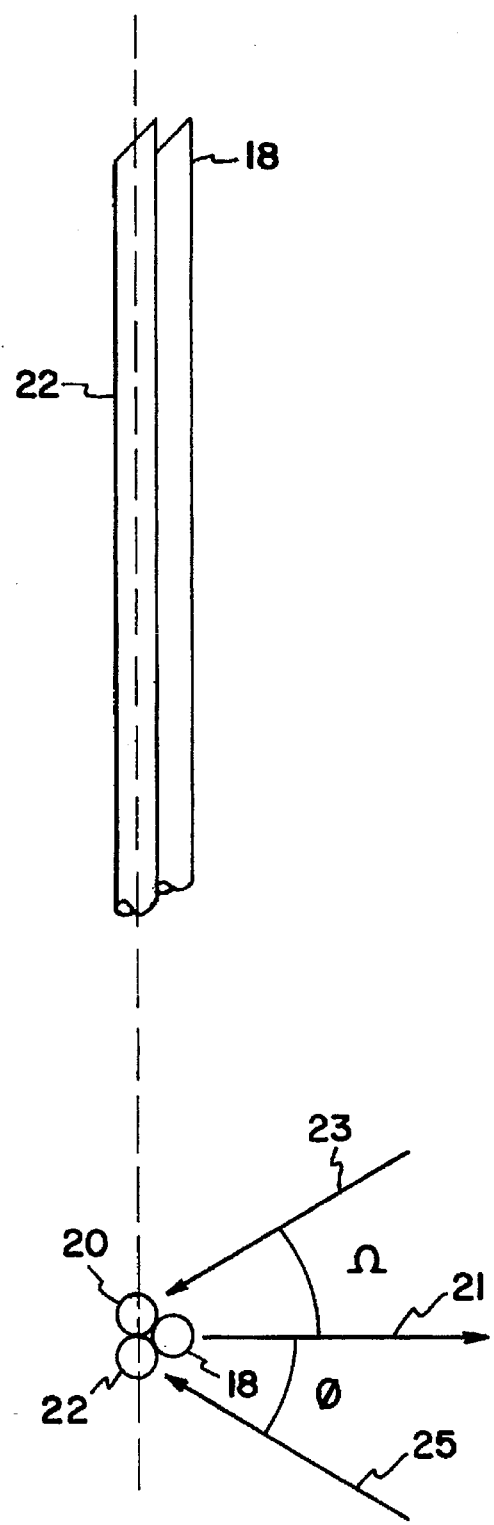
FIG. 4  FIG. 5

LASER DOPPLER OPTICAL SENSOR FOR USE ON A MONITORING PROBE

FIELD OF THE INVENTION

The present invention relates generally to an optical sensor or probe for measuring fluid flow, and more particularly to a laser Doppler blood perfusion monitoring probe for measuring blood flow in tissue.

BACKGROUND OF THE INVENTION

Blood flow is an important parameter which is measured as a part of certain surgical and diagnostic procedures. Laser Doppler flow meters utilize fiber optics to distribute coherent light to an anatomic site. The relative motion of the blood cells modulates the coherent light, and the frequency shift associated with the motion of the corpuscles can be extracted from a photodiode signal connected to a receiving fiber.

SUMMARY OF THE INVENTION

The probe of the present invention utilizes a single transmitting fiber connected to a source of laser light, and one or more receiving fibers which are connected to a photodiode detector. The distal ends of the fibers are cut to form facets. Each facet is then rendered reflective by metalization or the like, so that the light emerging from the transmit fiber leaves at an angle with respect to the fiber axis. One or more receive fibers are provided and each receive fiber is also cut at an angle to form a facet. This faceted geometry permits light scattered from tissue to be returned along an axis perpendicular to the long axis of the receive fiber. This creates a lateral or "side looking" sensor arrangement, which is useful in a variety of settings. The orientation of the fibers are important for the operation of the sensor, and it is generally desired to have the transmit fiber extend distally of the receive fibers and several configurations are contemplated. Although the unique sensor can be used in isolation, a sheath or cover may be applied to house the sensor for some applications.

BRIEF DESCRIPTION OF THE DRAWINGS

Throughout the several figures, like reference numerals refer to equivalent structure, wherein:

FIG. 2 is a schematic representation of an alternate configuration of the sensor;

FIG. 3 is a schematic representation of an alternate configuration of the sensor;

FIG. 4 is a schematic representation of an alternate configuration of the sensor; and, FIG. 5 is a schematic representation of an alternate configuration of the sensor.

DETAILED DESCRIPTION

Figure 1:
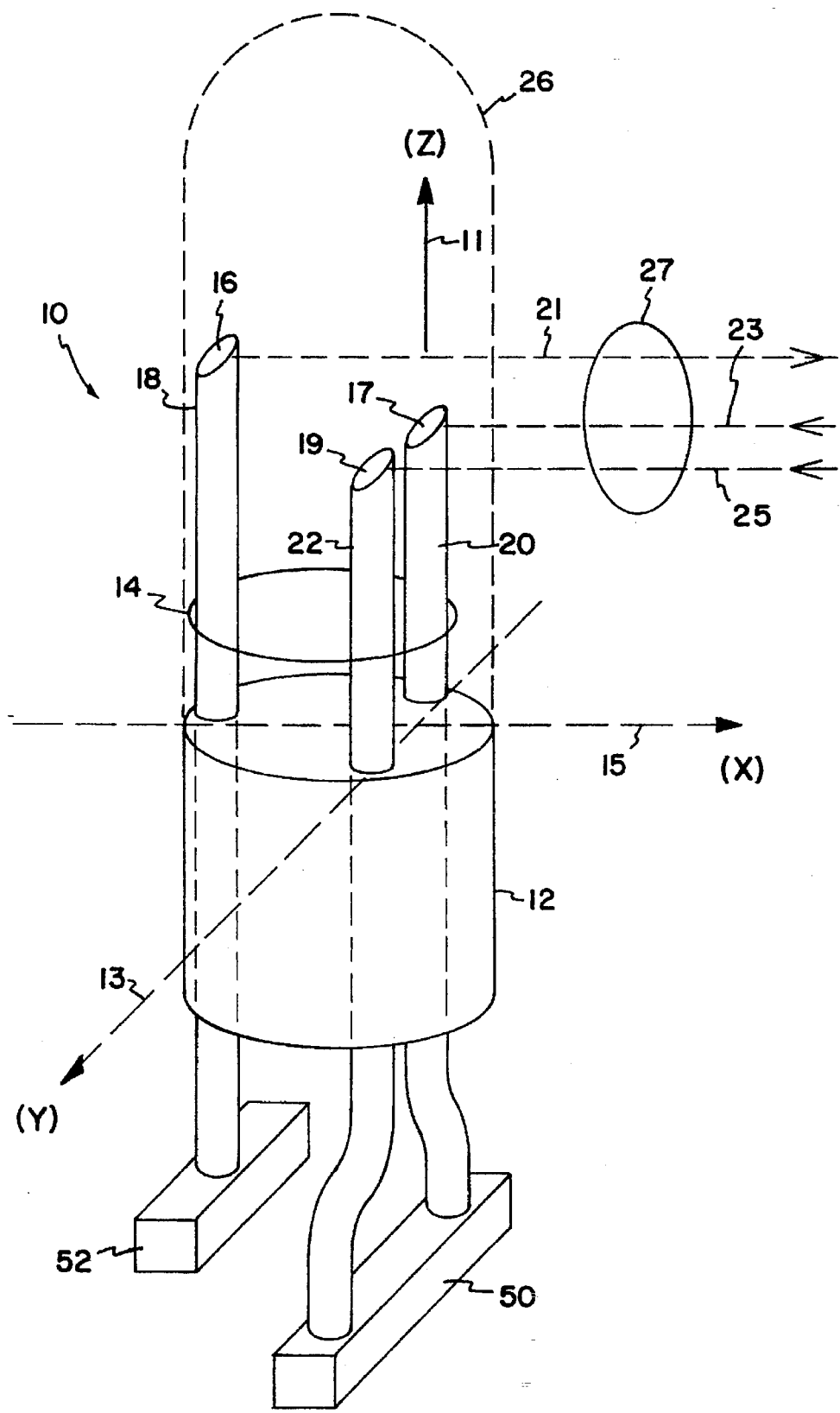
FIG. 1 is a schematic representation of the sensor.

FIG. 1 shows the blood perfusion probe 10 in a schematic fashion. The optical sensor assembly 14 is formed of a single transmit fiber 18, and one or more receive fibers. In the illustrative embodiment shown through out the figures a pair of receive fibers are shown as receive fiber 20 and receive fiber 22 respectively. It should be apparent that a single receive fiber is operable as well as embodiments which include three receive fibers. However for clarity in description only two receive fibers are shown in the various figures.

The two receive fibers are coupled to a photodetector 50, while the transmit fiber 18 is coupled to a source of optical radiation such as a laser 52. In this figure, three orthogonal directions are defined by coordinate 15 (X); the coordinate 13 (Y); and the coordinate 11 (Z). In the particular configuration depicted in FIG. 1 the two receive fibers lie in the YZ plane while the single transmit fiber 18 is displaced along the X axis from the plane of the receive fibers.

The distal tip of the transmit fiber 18 is cut to form a facet 16. The receive fibers typified by receive fiber 20 also are cut to form facets shown as facet 17 on fiber 20 and as facet 19 on fiber 22. The facets serve to direct light out of each fiber. For example the light is emitted from fiber 18 along the direction indicated by direction path 21. The light received by the receive fiber 20 enters along the centerline indicated by path 23. Similarly the light enters fiber 23 along the path shown as path 25. In each instance the centerline of the path is approximately orthogonal to the centerline or major axis of the fiber.

In general the single relatively small diameter (typically 50–100 µm, preferably 62.5 µm) transmit fiber 18, is positioned distal and "behind" the illustrative pair of relatively large diameter (typically 50–200 µm, preferably 100 µm) receive fibers shown as receive fiber 20 and receive fiber 22. The collective fiber orientation defines an aperture shown by the loop 27.

As seen in connection with FIG. 1, the fibers may be embedded in a transparent optical block 26, which stabilizes and retains the distal tips of the fibers in a fixed relationship with respect to each other. The optical block 26 may extend the entire length of the sheath 12 or the fibers may transition into a flexible fiber optic cable assembly as known in this industry. Although the optical sensor assembly 14 is shown in a schematic form for clarity, the fibers are typically embedded in the block 26 in optical epoxy to permanently position them. The optical sensor assembly 14 is then permanently covered by an extension of the sheath 12 to complete the fabrication of the probe 10.

FIG. 2 is a composite diagram showing a central sensor axis 29. This figure shows an elevation view and a plan view of an alternate fiber configuration. In this schematic diagram the transmit fiber 18 is "in front" of the plane defined by the two receive fibers shown as fiber 20 and fiber 22. In general, each fiber has a facet angle "theta" formed with respect to the central axis 29 which serves to direct light away from the central axis 29 as indicated by path arrow 31 for the transmit fiber 18 and path arrow 33 for the receive fiber 22.

A reflective coating 42 is provided at each oblique facet surface of each fiber. The preferred reflective coating is gold. Gold is preferred because of its high reflectivity at the wave lengths available for commercial laser sources. However silver is an alternative choice, and multilayer dielectric mirrors can also be formed on the distal facets to form a reflective mirror structure.

In general, the facet angle will be near forty five degrees but need not be equal to forty five degrees (forty five plus or minus 15 degrees for example). In the configuration of FIG. 1 the transmit facet angle "theta" will preferably be greater than forty five degrees, while in the configuration of FIG. 2 the transmit fiber facet angle will preferably be less than forty five degrees. In each of these examples the angle is selected to minimize internal reflection which returns light to the laser 52 which is undesirable. In general the configuration of FIG. 1 maximizes the amount of light emitted from the transmit fiber which improves overall system efficiency.

The relative displacement of the emitted light from fiber 18 and the received light from fiber 22, as determined by projecting the fibers on to a plane perpendicular to the path arrows 31 and 33 and measuring the distance between fibers 18 and 22 in this plane, is shown in FIG. 2 as the distance "D". This distance "D" may be selected to suit particular applications. It will preferably be approximately 0.5 mm, but may range from about 0.25 mm to 3.0 mm. In general, the depth of tissue which can be observed with the probe is a function of "D", with the identified range representing a compromise between laser power and tissue monitoring volume.

FIG. 3 shows an alternate and generally planar configuration where the transmit fiber 18 lies along the central axis 29 and is in the same plane as the receive fiber 20 and receive fiber 22. In this configuration the distance between the emitted light path and the received light path is shown as "L". In this configuration the preferred angle for the distal tip facet may be greater than or less than 45°. In this alternative configuration, all the fibers have the same length and are in the same plane.

In each of the foregoing embodiments it is generally preferred to have all the facets aligned to the same direction so that the beam centers of each facet are parallel to each other indicated in FIG. 4. However it should be understood that other alignments are possible as well. Although the configuration seen in FIG. 5 has the two receive fibers at an acute angle with respect to the transmit path 33, any angle from zero degrees to 360 degrees may be selected. This geometry may be especially useful where it is important to have as small a diameter probe as possible. In these instances the fibers will be clustered and abut each other in a minimum space filling configuration as seen in FIG. 5.

Although two specific applications of the sensor are shown it should be understood that the sensor can be used alone of integrated into a variety of devices without departing from the scope of the invention.

What is claimed is:

1. An optical sensor for use with an optical radiation source and a photo detector in a monitoring probe, comprising;

a transmit fiber having a proximal end and a distal end and having a central axis, said proximal end of said transmit fiber being configured for coupling to said optical radiation source;

a receive fiber, having a proximal end and a distal end and having a central axis, said proximal end of said receive fiber being configured for coupling to said photo detector;

said transmit fiber distal end being cut at an angle to said fiber axis forming a transmit facet;

said receive fiber distal end being cut at an angle to said fiber axis forming a receive facet;

a reflector formed on said transmit facet;

a reflector formed on said receive facet;

each of said reflectors aligned so that they lie in substantially parallel planes;

said transmit distal end and said receive distal end being spaced apart, whereby said receive fiber is capable of receiving back-scattered light, initially emitted by said transmit fiber.

2. The optical sensor of claim 1 wherein said transmit fiber and receive fiber are parallel to each other.

3. The optical sensor of claim 1 wherein:

each of said reflectors is aligned so that they lie in planes not parallel to each other.

4. A monitoring probe, comprising;

an optical radiation source;

a photo detector: and an optical sensor, comprising:

a transmit fiber having a proximal end and a distal end and having a central axis, said proximal end of said transmit fiber being coupled to said optical radiation source;

a first receive fiber, having a proximal end and a distal end and having a central axis, said proximal end of said first receive fiber being coupled to said photo detector;

a second receive fiber, having a proximal end and a distal end and having a central axis, said proximal end of said second receive fiber being coupled to said photo detector;

said transmit distal end being cut at an angle to said fiber axis forming a transmit facet;

said first receive distal end being cut at an angle to said fiber axis forming a first receive facet;

said second receive distal end being cut at an angle to said fiber axis forming a second receive facet;

a reflector formed on said transmit facet;

a reflector formed on said first receive facet;

a reflector formed on said second receive facet;

all of said reflectors lying in substantially parallel planes;

each of said fiber axes being substantially parallel; and said transmit distal end and said receive distal ends being spaced apart, whereby said first and second receive fibers are capable of receiving back-scattered light emitted by said transmit fiber.

5. The monitoring probe of claims 4 wherein:

said first receive fiber and said second receive fiber define a plane;

said transmit fiber is located proximate said plane and parallel to said plane but said transmit fiber does not lie in said plane.

6. The monitoring probe of claim 4 wherein:

said first receive fiber and said second receive fiber are of equal length;

said transmit fiber extending distal of the distal ends of each of said first receive fiber and said second receive fiber.

7. The monitoring probe of claim 4 wherein:

said first receive fiber and said second receive fiber are of equal length:

said transmit fiber extending proximal of the distal ends of each of said first receive fiber and said second receive fiber.

8. The monitoring probe of claim 4 wherein:

said first receive fiber and said second receive fiber and said transmit fiber lie in the same plane.

9. The optical sensor of claim 4 wherein:

each of said reflectors is aligned so that the planes containing the facets of said receive fibers are not parallel to the plane containing the facet of the transmit fiber.

* * * * *